US011950792B2

(12) United States Patent
Haworth et al.

(10) Patent No.: US 11,950,792 B2
(45) Date of Patent: Apr. 9, 2024

(54) INTRAVASCULAR ULTRASOUND DEVICE AND METHODS FOR AVOIDING OR TREATING REPERFUSION INJURY

(71) Applicants: University of Cincinnati, Cincinnati, OH (US); Children's Hospital Medical Center, Cincinnati, OH (US)

(72) Inventors: Kevin Haworth, Cincinnati, OH (US); Christy K. Holland, Cincinnati, OH (US); Karla Mercado-Shekhar, Cincinnati, OH (US); Andrew Redington, Cincinnati, OH (US); Bryan H. Goldstein, Cincinnati, OH (US)

(73) Assignees: University of Cincinnati, Cincinnati, OH (US); Children's Hospital Medical Center, Cincinnati, OH (US)

( * ) Notice: Subject to any disclaimer, the term of this patent is extended or adjusted under 35 U.S.C. 154(b) by 1150 days.

(21) Appl. No.: 16/614,584

(22) PCT Filed: May 18, 2018

(86) PCT No.: PCT/US2018/033298
§ 371 (c)(1),
(2) Date: Nov. 18, 2019

(87) PCT Pub. No.: WO2018/213657
PCT Pub. Date: Nov. 22, 2018

(65) Prior Publication Data
US 2020/0107844 A1 Apr. 9, 2020

Related U.S. Application Data

(60) Provisional application No. 62/509,313, filed on May 22, 2017, provisional application No. 62/508,650, filed on May 19, 2017.

(51) Int. Cl.
*A61B 17/22* (2006.01)
*A61K 9/107* (2006.01)
(Continued)

(52) U.S. Cl.
CPC .......... *A61B 17/2202* (2013.01); *A61K 9/107* (2013.01); *A61K 31/02* (2013.01);
(Continued)

(58) Field of Classification Search
CPC .......... A61B 17/22004; A61B 17/2202; A61B 17/22032; A61B 2017/00243;
(Continued)

(56) References Cited

U.S. PATENT DOCUMENTS 6,176,842 B1 1/2001 Tachibana et al.
2009/0112150 A1 4/2009 Unger et al.
2014/0004099 A1 1/2014 Culp et al.

FOREIGN PATENT DOCUMENTS

WO 2017035454 A1 3/2017

OTHER PUBLICATIONS

International Search Report and Written Opinion of corresponding PCT Application No. PCT/US2018/033298 dated Aug. 7, 2018.
(Continued)

*Primary Examiner* — Shefali D Patel
(74) *Attorney, Agent, or Firm* — Dinsmore & Shohl LLP

(57) ABSTRACT

An intravascular ultrasound (IVUS) catheter-based device for targeted delivery of ultrasound-activated emulsions of oxygen-scavenging droplets into a bloodstream of patients suffering from a hypoxic condition and methods utilizing the device to protect the patients from reperfusion injury upon restoration of oxygenated blood to a hypoxic tissue.

18 Claims, 8 Drawing Sheets

(51) Int. Cl.
*A61K 31/02* (2006.01)
*A61K 41/00* (2020.01)
*A61M 37/00* (2006.01)
*A61B 17/00* (2006.01)

(52) U.S. Cl.
CPC ..... *A61K 41/0028* (2013.01); *A61M 37/0092* (2013.01); *A61B 2017/00243* (2013.01); *A61B 2017/00778* (2013.01); *A61B 2017/22088* (2013.01); *A61M 2210/12* (2013.01)

(58) Field of Classification Search
CPC ........... A61B 2017/00778; A61B 2017/22027; A61B 2017/22034; A61B 2017/22051; A61B 2017/22067; A61B 2017/22088; A61B 5/14; A61B 5/145; A61B 5/14503; A61B 5/14542; A61B 5/14551; A61B 5/1459; A61B 5/4836; A61B 5/4839; A61B 5/4848; A61B 5/6846; A61B 5/6847; A61B 5/6852; A61B 5/6853; A61B 5/6862; A61B 5/6876; A61K 31/02; A61K 41/0028; A61K 9/107; A61M 2205/33; A61M 2205/3327; A61M 2205/50; A61M 2210/12; A61M 2230/20; A61M 2230/205; A61M 25/10; A61M 37/0092; A61M 2202/0208; A61M 2202/0476
See application file for complete search history.

(56) References Cited

OTHER PUBLICATIONS

Michael J. Haas, Analysis: Targets and Mechanisms—Hematology; Craft Air Carrier Science-Business Exchange May 29, 2012.

Fig. 4

Table 1

| Tukey's multiple comparisons test | Mean Diff. | 95.00% CI of diff. | Adjusted P Value |
|---|---|---|---|
| Baseline:Sham vs. Baseline:Ultrasound | -0.3673 | -12.14 to 11.4 | >0.9999 |
| Baseline:Sham vs. Droplets Added:Sham | 13.99 | 2.218 to 25.76 | 0.0134 |
| Baseline:Sham vs. Droplets Added:Ultrasound | 13.56 | 1.792 to 25.34 | 0.0174 |
| Baseline:Sham vs. Treatment:Sham | 20.91 | 9.136 to 32.68 | 0.0002 |
| Baseline:Sham vs. Treatment:Ultrasound | 97.4 | 85.62 to 109.2 | <0.0001 |
| Baseline:Ultrasound vs. Droplets Added:Sham | 14.36 | 2.585 to 26.13 | 0.0107 |
| Baseline:Ultrasound vs. Droplets Added:Ultrasound | 13.93 | 2.16 to 25.7 | 0.0139 |
| Baseline:Ultrasound vs. Treatment:Sham | 21.28 | 9.503 to 33.05 | 0.0001 |
| Baseline:Ultrasound vs. Treatment:Ultrasound | 97.76 | 85.99 to 109.5 | <0.0001 |
| Droplets Added:Sham vs. Droplets Added:Ultrasound | -0.4253 | -12.2 to 11.35 | >0.9999 |
| Droplets Added:Sham vs. Treatment:Sham | 6.918 | -4.854 to 18.69 | 0.4742 |
| Droplets Added:Sham vs. Treatment:Ultrasound | 83.41 | 71.63 to 95.18 | <0.0001 |
| Droplets Added:Ultrasound vs. Treatment:Sham | 7.344 | -4.428 to 19.12 | 0.4099 |
| Droplets Added:Ultrasound vs. Treatment:Ultrasound | 83.83 | 72.06 to 95.6 | <0.0001 |
| Treatment:Sham vs. Treatment:Ultrasound | 76.49 | 64.71 to 88.26 | <0.0001 |

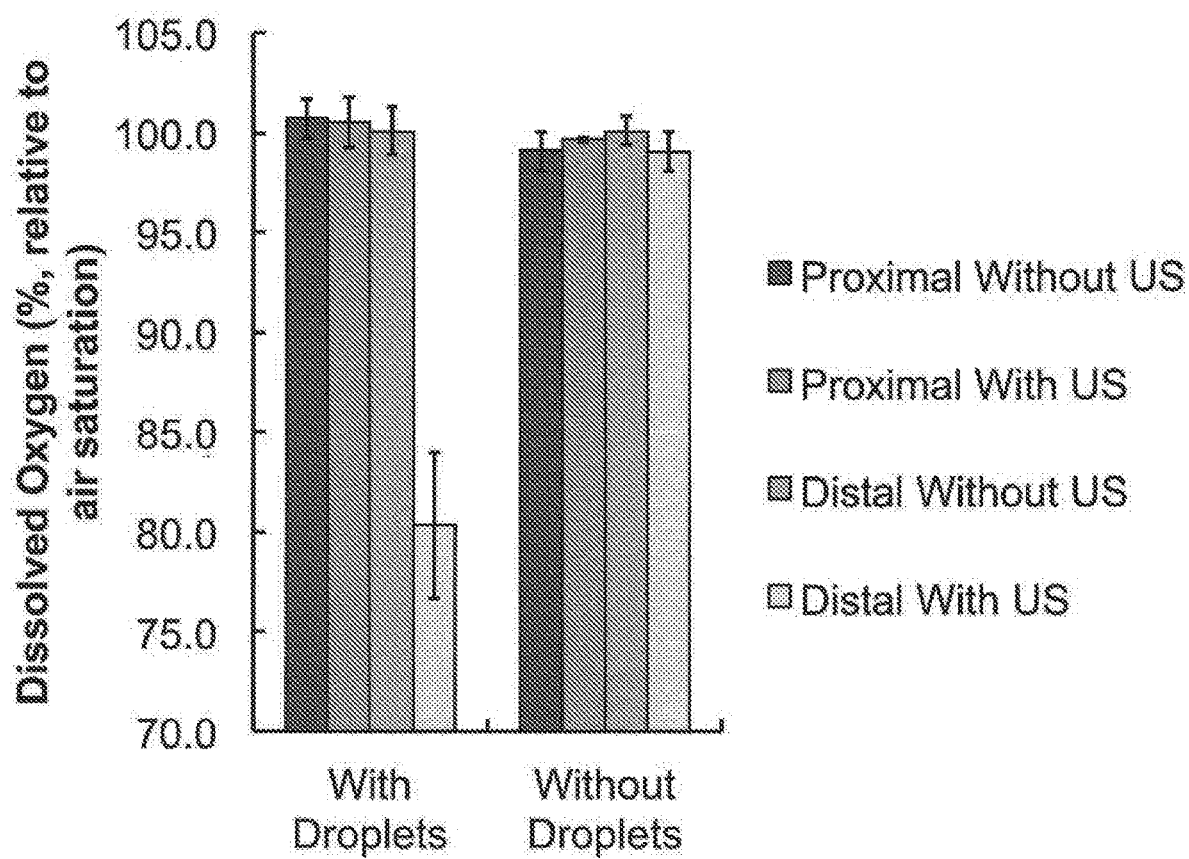

INTRAVASCULAR ULTRASOUND DEVICE AND METHODS FOR AVOIDING OR TREATING REPERFUSION INJURY

PRIORITY CLAIM

This application is a national stage application under 35 U.S.C. § 371 of International Application No. PCT/US2018/033298, filed May 18, 2018, and claims priority to U.S. provisional application Ser. No. 62/508,650 filed May 19, 2017, and Ser. No. 62/509,313, filed May 22, 2017, the entire disclosures of which are incorporated herein by reference.

GOVERNMENT LICENSE RIGHTS

This invention was made with government support under K25HL133452 awarded by National Institutes of Health. The government has certain rights in the invention.

BACKGROUND

Modification of dissolved gas content by nucleation of acoustic droplet vaporization (ADV), the ultrasound-mediated phase transition of perfluorocarbon droplets into gas microbubbles, has been studied for over two decades and has been more recently proposed for several therapeutic applications. Several groups of investigators have noted that following the phase-transition of perfluorocarbons from a liquid to a gas, other dissolved gases (e.g. nitrogen and oxygen) diffuse into the microbubbles. The concomitant reduction of dissolved oxygen (DO) in the surrounding fluid is due to a difference in the partial pressures in the perfluorocarbon microbubble and the surrounding fluid consequent to ADV.

Reperfusion (reoxygenation) injury is the tissue damage caused when blood supply returns to the tissue after a period of ischemia or lack of oxygen (anoxia, hypoxia). The absence of oxygen and nutrients from blood during the ischemic period creates a condition in which the restoration of circulation results in inflammation and oxidative damage through the induction of oxidative stress rather than restoration of normal function. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. White blood cells may also bind to the endothelium of small capillaries, obstructing them and leading to more ischemia. It is also possible that normally, tissues contain free radical scavengers to avoid damage by oxidizing species normally contained in the blood. Ischemic tissue would have a decrease in function of these scavengers because of cell injury.

Once blood flow is reestablished, oxygen species contained in the blood will damage the ischemic tissue because the function of the scavengers is decreased. Thus, reducing dissolved oxygen could inhibit reactive oxygen species production during reperfusion, substantially ameliorating or even preventing reperfusion injury if initiated immediately upon an increase in DO, or even upon a contemplated increase in DO. In particular, the ability to prevent reperfusion injury after restoration of oxygen to ischemic tissue such is a compelling need in the art.

SUMMARY

Accordingly, Embodiments of the invention provide methods that utilize an intravascular ultrasound (IVUS) device to reduce dissolved oxygen in a blood flow by acoustic droplet vaporization, and to prevent or substantially reduce reperfusion injury in patients suffering from a hypoxic condition and about to undergo or undergoing reperfusion therapy.

One embodiment is directed to methods for protecting a patient suffering from a hypoxic condition against reperfusion injury, the method comprising: delivering an emulsion into a blood vessel of a patient via a catheter-based system; and activating the emulsion prior to or subsequent to delivery by application of intra-vascular ultrasound, such that the activated emulsion scavenges dissolved oxygen present in blood flowing in the blood vessel.

One embodiment provides an intravascular ultrasound catheter for the targeted delivery of ultrasound-activated gas-scavenging emulsions to a blood flow having either an elevated dissolved oxygen level or contemplated for having an elevated dissolved oxygen level, the catheter comprising at least one ultrasound transducer and at least one port distal or proximal, or in the case of multiple ports, either or both, to the transducer for exit of the ultrasound-activated gas-scavenging emulsion into the vascular lumen. The device is further capable of being combined with existing conventional intravascular devices for the treatment of, for example, occluded vessels such that upon clearing of a clot and consequent reperfusion, injury to previously hypoxic tissue is minimized.

One embodiment provides a catheter-based system for targeted delivery of ultrasound-activated gas-scavenging emulsions, the system comprising, an intravascular ultrasound catheter comprising at least one ultrasound transducer and at least one port distal to the transducer for exit of the ultrasound-activated emulsion, and further comprising a pump for introducing the emulsion into the catheter, at least one sensor located in the vascular lumen to detect a level of dissolved oxygen, wherein the sensor may be located proximal or distal to an emulsion exit port, and a control unit for monitoring feedback from the at least one sensor and adjusting one or more of a droplet flow rate, an average droplet size, and parameters of activating ultrasound in response thereto.

These and other embodiments and aspects will be further clarified by reference to the Figures and Detailed Description below.

The Figures are provided to illustrate certain underpinning concepts and to exemplify specific embodiments and should not be construed as limiting the scope of the invention as defined by the appended claims.

BRIEF DESCRIPTION OF THE FIGURES

FIG. 2A shows showing that distal to the IVUS catheter is relatively hypoechoic without IVUS exposure; FIG. 2B shows that with IVUS exposure the lateral location of the element can be identified from the passive cavitation image. Hyperechoic ADV microbubbles are observed distally.

FIG. 4: sets fort data generated in Example 3 as Table 1 showing the differences and p-values for a 2-way ANOVA comparing all experimental groups.

FIG. 7: Dissolved oxygen was measured by two sensors in the flow system. One sensor was located upstream of ultrasound transducer and the other sensor was located downstream. In the absence of the emulsion in the flow system, the dissolved oxygen content of the saline was the same upstream and downstream with and without ultrasound exposure. When the emulsion was added to the flow in the absence of ultrasound exposure, the dissolved oxygen content did not change. When the emulsion was exposed to ultrasound, the dissolved oxygen content of the downstream fluid decreased.

DETAILED DESCRIPTION

Figure 1:
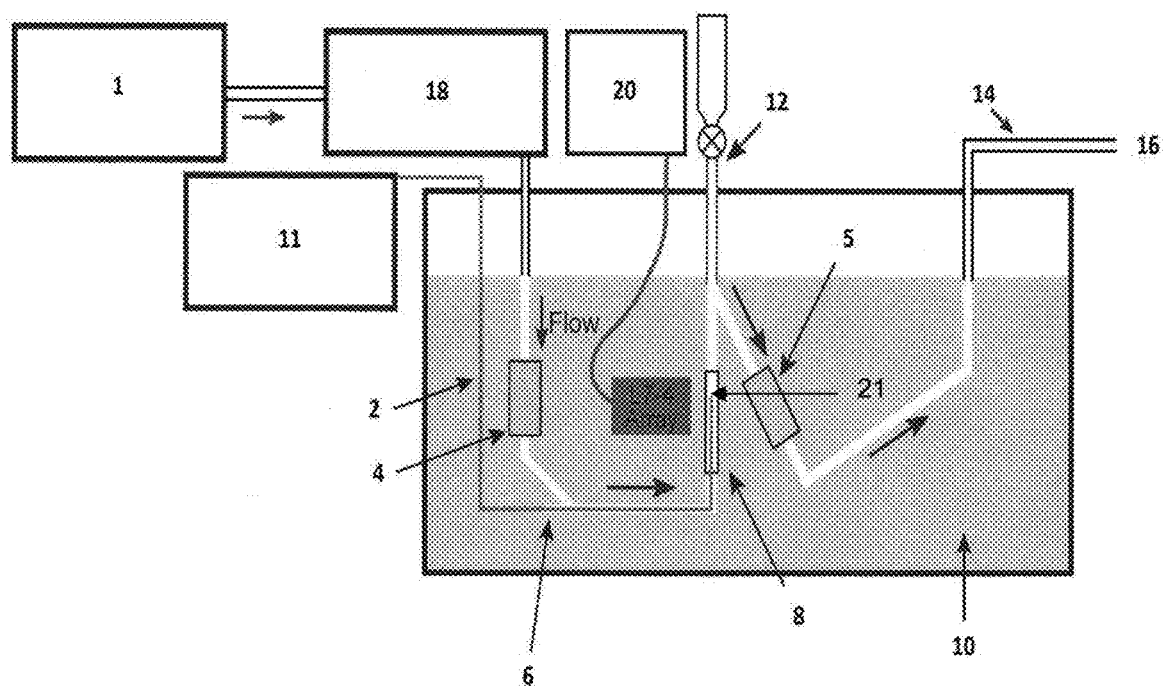
FIG. 1: Illustrative schematic of a flow phantom used to assess the ability of an intravascular ultrasound device (catheter) operating at 40 MHz to nucleate acoustic droplet vaporization and gas scavenging.

The present investigators previously disclosed a technique (see PCT/US16/48934, the entire disclosure of which is incorporated herein by this reference) for scavenging dissolved gases from a liquid using an ultrasound-activated emulsion. In the present a novel IVUS device designed, for example, to be integrated with catheter-based intra-vascular devices utilized for imaging during intra-arterial procedures, is provided for delivering and activating an emulsion comprising droplets.

One embodiment is directed to methods for protecting a patient suffering from a hypoxic condition against reperfusion injury upon restoration of oxygen to hypoxic tissue. The methods comprise: delivering an emulsion into a blood vessel of a patient via a catheter-based system; and activating the emulsion prior to or subsequent to delivery by application of intra-vascular ultrasound, such that the activated emulsion scavenges dissolved oxygen present in blood flowing in the blood vessel. Examples of hypoxic conditions that subject a patient to a risk of tissue damage from reperfusion include a) coronary ischemic occlusion; b) myocardial infarction; c) cerebral ischemic occlusion; d) ischemic stroke; e) peripheral arterial disease; f) transplant procedure; g) crush injury; h) deep vein thrombosis; i) pulmonary embolism; and h) a medical procedure that required temporary partial or complete hemostasis. According to some embodiments, DO sensors provide feedback to a control unit such as a computer in order to maintain the DO of the patient at a desired level. The ultrasound energy and/or the concentration of droplets and/or the rate of droplet delivery may be adjusted to keep the DO at the desired level.

One embodiment is directed to a catheter for the targeted delivery of ultrasound-activated gas-scavenging emulsions, the catheter being sized for insertion into a target vascular lumen and comprising: at least one ultrasound transducer, and at least one port distal to the transducer for exit of an ultrasound-activated emulsion into the vascular lumen. According to specific embodiments, the catheter and catheter system can be implemented either with or without other catheter-based features that may be used for alleviating ischemic conditions. Such features could include, for example, a balloon for angioplasty, a stent deployment system, or mechanical embolectomy features. The total diameter of the catheter would have dimensions to allow it to be placed into the vessel containing the obstruction (e.g., a coronary artery, pulmonary artery, or cerebral artery, or a peripheral vessel).

A catheter-based system is provided for targeted delivery of ultrasound-activated gas-scavenging emulsions, the system comprising an IVUS catheter embodiment and further comprising a pump for introducing the emulsion into the catheter, at least one sensor located in the vascular lumen to detect a level of dissolved oxygen (DO), wherein the sensor may be located in the blood flow proximal or distal to the emulsion exit port of the catheter, and a control unit for monitoring feedback from the at least one sensor and adjusting one or more of a droplet flow rate, an average droplet size, droplet concentration, and parameters of the activating ultrasound in response thereto. For example if DO levels dip below a desired level, the flow rate of the scavenging microbubbles/droplets may be reduced, or the activating ultrasound may be reduced or turned off intermittently. On the other hand, if the DO rises to potentially injurious levels the droplet delivery rate or concentration may be increased, or the ultrasound energy may be adjusted to increase activation efficiency. The device and methods make it possible to maintain desired DO in the blood flow at desired levels for the patient to avoid reperfusion injury while restoring normal oxygen levels to hypoxic tissue.

The advantages of a catheter-based system are that 1) it eliminates the need for complex targeting of the ultrasound field to activate the emulsion only in the desired vessel, 2) it can be integrated into existing catheterization procedures that are commonly used to treat ischemic conditions such as myocardial infarction and ischemic stroke, and 3) it can allow for simultaneous delivery of the emulsion specifically to the target vessel and precise local ultrasound activation via the existing catheterization procedure.

The ultrasound-activation may be performed by a single-element transducer on the catheter or an array of elements on the catheter. According to one specific embodiment, the droplets may flow around the transducer(s) or, in other embodiments, the transducer may have a hole within it (e.g., a ring), through which the emulsion flows, or both. According to specific embodiments, the device utilizes frequencies between 500 kHz and 60 MHz. The ultrasound insonation duration may vary from one-half cycle to continuous wave and may be pulsed, intermittent, comprise rest periods of zero ultrasound energy over a time interval, or may be continuous. The repetition rate of the ultrasound insonation may vary from 1 microsecond to 1 second. The insonation pressure amplitudes may vary from 100 kPa to 25 MPa.

Where ranges are provided herein, all values and sub-ranges between and including the stated values are intended to be included.

The emulsion may be administered into the blood stream intravenously (e.g., systemic delivery) or through a port in the catheter, a guide catheter, or a long sheath used to insert the catheter for targeted delivery. The port opening into the blood stream may be proximal or distal to the ultrasound transducer(s) used to activate the emulsion. If the port is distal to the ultrasound transducer(s), then the emulsion may be activated before leaving the catheter. The droplets may be infused at a rate of $10^3$ droplets/s to $10^{12}$ droplets/s, and flow rates in between. Generally, as droplet size decreases, flow rate increases, and vice versa. The infusion volumetric flow rate may vary from 1 mL/min to 2 L/min. According to specific embodiments, the infused droplets comprise a perfluorocarbon core, in which the perfluorocarbon has a bulk boiling point below 60 degrees Celsius. The perfluorocarbon core may be composed of a single perfluorocarbon species or an admixture of perfluorocarbon species. Exemplary perfluorocarbons include (but are not limited to) perfluorohexane, perfluoropentane, perfluoropropane, or perfluorobutane. According to specific embodiments, the core may also be composed of condensed sulfur hexafluoride.

Figure 3:
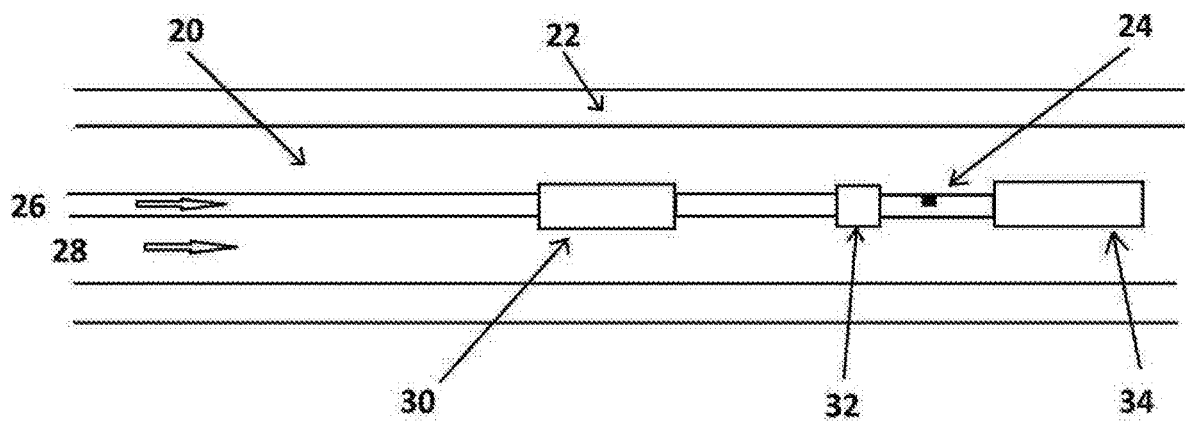
FIG. 3: Sets forth an illustrative system embodiment. The shaft of the catheter is shown in gray. The catheter may be of variable length. The catheter, at a minimum, comprises the ultrasound transducer that activates the emulsion and gas scavenging process. According to this specific embodiment, a balloon and stent are shown, which may be used to mechanically open the vessel lumen to restore flow. Additionally, an embolectomy device is shown that can be used to remove emboli. A port is shown distal to the ultrasound transducer to enable the emulsion to be injected through the shaft, activated by the ultrasound transducer, and then delivered via flow into the blood stream.

A very specific embodiment of an IVUS catheter device is illustrated schematically in FIG. 3. The device is inserted into the vascular lumen 20 and the direction of the blood flow 28 is the same as the direction of the infusion flow 26. Specific embodiments may have one or more US transducers 32 positioned prior to the port where the emulsion is introduced into the blood stream 24, or in some specific embodiments, an array of transducers may be present. Option components include balloon and stent deployment 30 and embolectomy components 34. Other embodiments are also possible, such as switching the placement of the different components (e.g., moving the port to be distal to the ultrasound transducer), excluding some of the components (e.g., the embolectomy component), or including multiples of one or more components (e.g., having multiple ultrasound transducers and/or ports). The port for emulsion introduction may be integrated directly into the catheter or may be incorporated into the system through a second catheter, such as a guide catheter or a long sheath. The port may also be designed to enhance the mixing of the activated emulsion with the blood to accelerate the rate of oxygen scavenging. Two necessary components are at least one port for introducing the emulsion into the blood stream and at least one ultrasound transducer to nucleate the emulsion phase transition and oxygen scavenging.

Figure 2A:
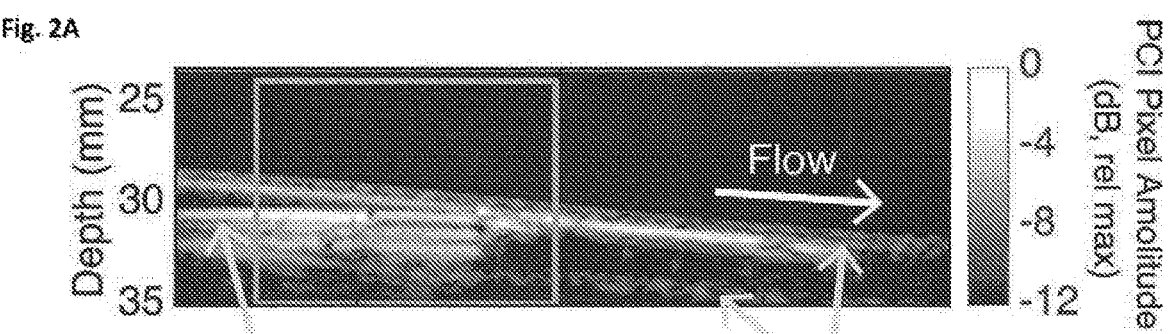
FIGS. 2A and 2B: Duplex B-mode and Passive Cavitation Image of the flow phantom tube with the IVUS catheter inserted; droplets flowed through the shaft and were activated by the US transducer and the emulsion flowed out of the catheter shaft and mixed with the flowing saline.
Figure 2B:
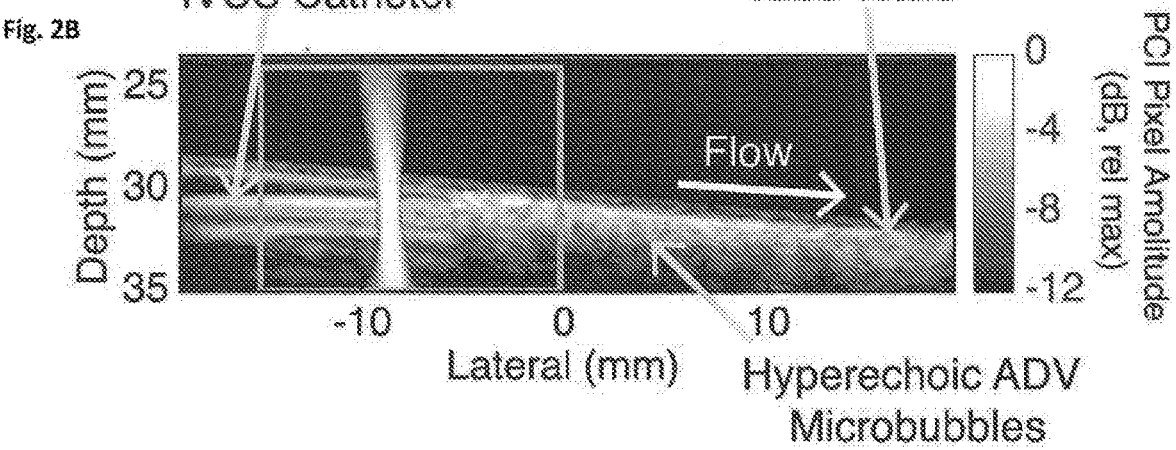

Transverse B-mode images of the phantom and IVUS catheter with droplets infused are shown in FIG. 2A and FIG. 2B with and without IVUS acoustic output, respectively. The color map shows the location of acoustic emissions. Microbubbles are visible downstream from the IVUS transducer, indicating that ADV was nucleated. The measured dissolved oxygen for the upstream and downstream dissolved oxygen sensors are shown in FIG. 7. A 20% decrease in dissolved oxygen was measured downstream of the IVUS transducer only when perfluoropentane droplets are infused. Modeling predicted a 20% reduction in dissolved oxygen corresponds to phase-transitioning 0.001% (v/v) of the infused fluid. The results set forth in the Examples below demonstrate that a reduction of dissolved oxygen by ADV is feasible from a clinical IVUS system.

Example 1

The following Example demonstrates that an off-the-shelf clinical coronary IVUS system is capable of nucleating ADV to induce oxygen scavenging.

A. Droplet Manufacturing

1) High-Speed Shaking

Droplets were manufactured using high speed shaking as previously described. Briefly, 0.25 mL (0.425 g) of perfluoropentane (FluoroMed, Round Rock, USA) was added gravimetrically to a 2 mL serum vial. Subsequently, 0.75 mL of 4 mg/mL bovine serum albumin (Sigma-Aldrich, St. Louis, USA) in 0.01 M phosphate-buffered saline (PBS, Sigma-Aldrich) was added and the vial was capped, crimped, and shaken at 4800 RPM for 30 s (Wig-L-Bug, Dentsply Rinn, York, USA). Droplets were stored at 5° C. between 12 hours and 7 days. Prior to use, large droplets were removed using centrifugation. Initially, 1 mL of the droplet emulsion was added to 3.8 mL of PBS in a 15 mL conical centrifuge tube and centrifuged for 1 min at 70×g. Of the supernatant, 3.456 mL was reserved and centrifuged for 5 min at 5000×g. 1.310 mL of the pellet was reserved and resuspended in PBS. The droplet concentration and size distribution were measured using a Multsizer 4 Coutler counter (Beckman Coulter Inc., Brea, USA).

2) Microfluidic Manufacturing

Droplets were extruded using a microfluidic chip (Dolomite, Royston, United Kingdom) with 14 μm×17 μm channels similar to the methods described previously. The chip has three inlet ports. The center inlet port had perfluoropentane pumped through it at a flow rate of 1 μL/min. The two outer ports were infused with a 62.5 mg/mL solution of Pluronic F68 (CAS #9003-11-6, Sigma-Aldrich) in PBS at a flow rate of 5.5 μL/min. Droplets were collected from the outlet and sized with a Multsizer 4 Coulter counter.

B. Ultrasound Exposure Systems

Droplets were exposed to ultrasound using a clinical coronary IVUS system (iLab, Boston Scientific, Marlborourgh, USA) in either a sample holder with static fluid or a flow phantom. DO was measured before and after ultrasound exposure using DO sensors (Pyroscience GmbH, Aachen, Germany).

1) Flow Phantom

A schematic of the flow phantom is shown in FIG. 1. PBS at 37° C. 1 was pumped through the flow phantom at 8.5 mL/min using a peristaltic pump 18. High-speed shaken and centrifuged droplets were injected into the system using a syringe pump 11 at 1.5 mL/min via the flush port of the intravascular (IVUS) catheter 2 (Opticross®, 3.0 Fr, 40 MHz coronary imaging catheter, Boston Scientific). The total volumetric flow rate exiting the system through the opening 21 was 10 mL/min. The 40.3 MHz IVUS transducer was driven using an iLab system and had a manufacturer-reported derated peak negative pressure of 1.37 MPa at a distance of 0.75 mm from the transducer(location of maximum intensity). Flow-through DO sensors (Pyroscience GmbH) were placed proximal 4 and distal 5 to the active element of the IVUS transducer. A bubble trap 12 was placed proximal to the second (distal) DO sensor 5 as large numbers of microbubbles were observed to interfere with the optics of the DO sensor. ADV was monitored using both B-mode imaging and passive cavitation imaging with an L7-4 linear array (Philips, Bothell, USA) connected to a Vantage 256 ultrasound research scanner 20 (Verasonics, Kirkland, USA). Passive cavitation images were formed using a delay, sum, and integrate algorithm. Summation was performed over the frequency band of 2-6 MHz to identify the location of NUS emissions. An increase in echogenicity was used to confirm ADV.

2) Static Exposure System.

Droplets manufactured with microfluidics were phase-transitioned using the same IVUS catheter. Droplets were diluted in static PBS to a volumetric concentration of $6.0 \times 10^8$ $\mu m^3/mL$ (0.06% v/v). One milliliter of the diluted droplet solution was reserved in a 15 mL centrifuge tube as a non-IVUS exposed control. The other 1 mL was slowly drawn into a 6.0 Fr guide catheter. The IVUS catheter (3.0 Fr) was inserted into the guide catheter, the acoustic output was turned on and was passed through the guide catheter 6 times. The fluid in the guide catheter was slowly withdrawn into a 1 mL syringe, minimizing exposure to the air. The DO of the IVUS exposed sample and non-IVUS exposed control were measured for approximately 30 s using a needle DO sensor (OXR430-UHS, Pyroscience GmbH).

C. Results

1) Droplet Size Distributions

Figure 8:
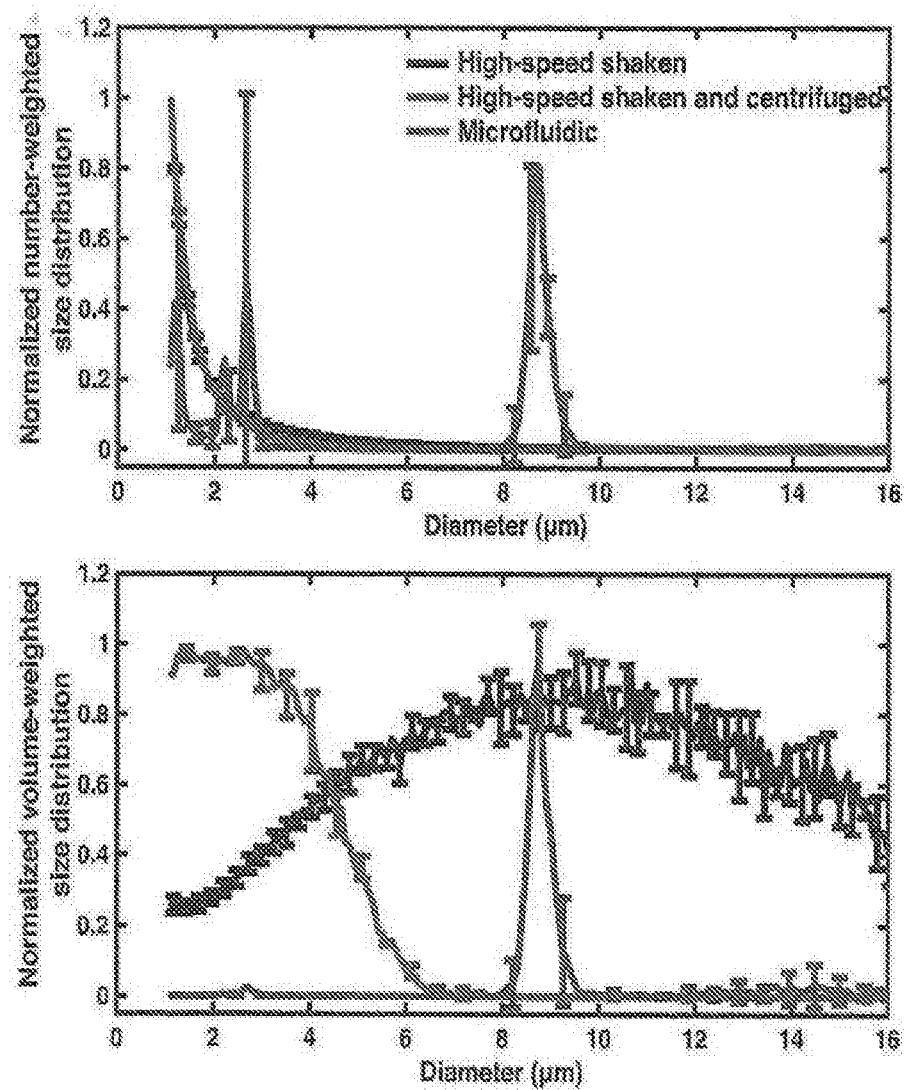
FIG. 8: Normalized number-weighted (top) and volume-weighted (bottom) size distribution of the droplets manufactured via high speed shaking (black), high-speed shaking with size isolation via centrifugation, and microfluidic manufacturing techniques.

The normalized number-weighted and volume-weighted size distributions of the droplets are shown in FIG. 8. The magnitude of DO scavenging is dependent on the total volume of perfluoropentane phase-transitioned. For reference, the size distribution of droplets manufactured using high-speed shaking but before centrifugation (black) are shown in addition to the size-isolated droplets and the droplets manufactured with a microfluidic chip. High-speed shaking produced droplets ranging from less than 1 µm in diameter to greater than 16 µm in diameter. A centrifugation protocol removed droplets greater than approximately 6 µm in diameter. The volume fraction of perfluoropentane droplets in PBS before centrifugation was $3.9 \times 10^{10}$ $\mu m^3/mL$ and $7.1 \times 10^9$ $\mu m^3/mL$ after centrifugation. Centrifugation results in 82% of the perfluoropentane volume lost.

In contrast, microfluidic droplet manufacturing resulted in a narrower droplet size distribution between approximately 8.0 µm and 9.6 µm in diameter. Thus, subsequent size-isolation was not needed and the corresponding loss did not occur. The number and volume fractions of perfluoropentane droplets in PBS collected from the effluent of the microfluidic chip was $1.53 \times 10^8$ droplets/mL and $6.42 \times 10^{10}$ $\mu m^3/mL$, respectively. Sufficient quantities of droplets could be produced for all the static experiments in under 2 h of manufacturing time.

2) IVUS-Nucleated ADV

Transverse B-mode images of the flow phantom and IVUS catheter with droplets infused are shown in FIG. 2A and FIG. 2B with and without IVUS acoustic output, respectively. Overlaid passive cavitation images show the beam formed acoustic emissions using a color map. Hyper-echogenic microbubbles are visible distal to the IVUS transducer only when exposed to ultrasound, indicating that ADV was nucleated 3) Dissolved Oxygen Scavenging 1) Flow Phantom The dissolved oxygen content of the fluid was measured in both the proximal and distal sensors for three trials with droplets and two trials without droplets. The average DO content measured by each sensor for each experimental condition is shown in FIG. 7. For all trials with droplets, a decrease in DO was measured by the distal sensor approximately 10 s after the IVUS was initiated, which was the time needed for the converted droplets to flow from the IVUS transducer to the DO sensor. When droplets were not present in the fluid, the DO did not change significantly when the IVUS acoustic output was turned on. For all trials, the proximal DO sensor did not detect a substantial change in DO for the duration of the experiments.

2) Static Exposure System

The DO content of the fluid not exposed to IVUS was 91.6%±0.2% (relative to air saturation). The DO content of the fluid exposed to IVUS was 80%±4%. The reduction in DO was significantly different based on a Student's t-test (p=0.02).

Example 2

The following Example demonstrates a second model demonstrating that an IVUS catheter device induces ADV and gas scavenging.

Catheters designed for ultrasound-assisted thrombolysis are known in the art. An exemplary such catheter is an EKOS® catheter manufactured and distributed by BTG Interventional Medicine. 9 mL of 3C $H_2$ (air-saturated by shaking) was added to each of two different 7.5 cm long, 1 cm inner diameter polystyrene tubes. The dissolved oxygen (DO) content was measured in both tubes using a needle DO sensor. 300 µL of resuspended non-size isolated droplets were then added to each tube. The tubes were gently inverted 2-3 times to mix the droplets uniformly in the tube. This yields a dilution of 1:30. The DO in each tube is measured again. One of the tubes is then exposed to an EkoSonic catheter transmitting 4 ms long pulses at 2.2 MHz and a 27 Hz PRF. The catheter is driven by 47 W of electrical power. The system was run for 30 s, however, there was ~12 s of initialization time when no ultrasound was transmitted. The DO was measured immediately after US exposure. 5 Trials were performed.

Results

Figure 5:
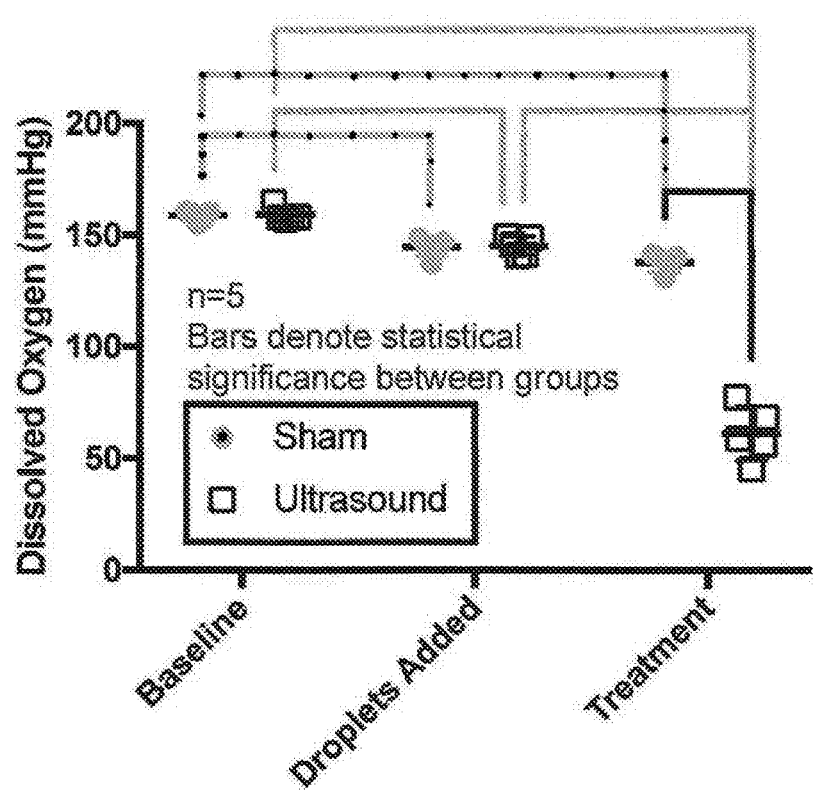
FIG. 5: a plot of results of Example 3 showing and comparing the average dissolved oxygen measured in the sham and Ultrasound cases at baseline (pre-droplets), after droplets but pre-treatment, and after treatment via catheter.
Figure 6A:
FIG. 6A: two experimental tubes at pre-ultrasound showing the catheter in the right tube.
Figure 6B:
FIG. 6B: the same tubes mid-way through treatment.

The production of microbubbles in the fluid was clearly visually observable, indicating ADV occurred. The bubbles appeared to be coming from the entire radius of the tube, meaning they were not just limited to nucleation on the catheter or on the polystyrene wall. FIG. 6A shows two tubes before is activation. The catheter can be observed in the right tube. FIG. 6B picture shows the tubes mid-way through treatment. IT is hard to observe due to low picture quality, but bands of bubbles that corresponded to the spacing of the transducers can be seen. The large number of bubbles produced also created a foam that can be seen at the top of the tube. When the dissolved oxygen was measured after US exposure (or sham), the DO values appeared steady. The plot set forth in FIG. 5 shows the average DO measured in the sham and US cases at baseline (pre-droplets), after droplets but pre-treatment, and after treatment (US or sham). Adding droplets decreased the DO slightly, but the difference was significant. There was no difference between the Sham and ultrasound cases at baseline or after adding droplets. There was no difference between after adding droplets and after sham treatment. There was a statistically significant difference between ultrasound treatment and all other groups. Table 1, FIG. 4 shows the differences and p-values for a 2-way ANOVA comparing all experimental groups. Overall, a very robust gas scavenging effect is observed. In terms of DO %, the change was from ~90% to 39%.

Embodiments of the invention provide clinical IVUS device and methods utilizing the IVUS device to scavenge oxygen and exploit ADV to avoid/substantially prevent reperfusion injury at the time of transcatheter treatment of ischemia-reperfusion syndromes.

The invention claimed is:

1. A method for protecting a patient suffering from a hypoxic condition against reperfusion injury, the method comprising: inserting a catheter of a catheter-based system into a target blood vessel of the patient; delivering a perfluorocarbon emulsion into the catheter of the catheter-based system; activating the perfluorocarbon emulsion within the catheter of the catheter-based system by application of intra-vascular ultrasound; and delivering the activated perfluorocarbon emulsion to the target blood vessel of the patient to allow the activated perfluorocarbon emulsion to scavenge dissolved oxygen present in blood flowing in the target blood vessel.

2. The method according to claim 1, wherein the perfluorocarbon emulsion comprises droplets comprising a perfluorocarbon core, said core comprising perfluorohexane, perfluoropentane, perfluoropropane, perfluorobutane, or a combination thereof.

3. The method according to claim 2, wherein the droplets are optimized for size, flow rate, and concentration.

4. The method according to claim 3, wherein the droplets have an average diameter of less than 8.9 µm.

5. The method according to claim 1, wherein the hypoxic condition is selected from a) a coronary ischemic occlusion; b) a myocardial infarction; c) a cerebral ischemic occlusion; d) an ischemic stroke; e) a peripheral arterial disease; f) a transplant procedure; g) a crush injury; h) a deep vein thrombosis; i) a pulmonary embolism; and h) a medical procedure that required temporary partial or complete hemostasis.

6. The method according to claim 1, wherein the ultrasound application is performed by one or more transducers located on the catheter of the catheter-based system.

7. The method according to claim 6, wherein the one or more transducers comprise an opening through which the perfluorocarbon emulsion flows.

8. The method according to claim 6, wherein the perfluorocarbon emulsion flows around the one or more transducers.

9. The method according to claim 1, wherein the ultrasound application comprises providing ultrasound frequencies between 500 kHz and 60 MHz.

10. The method according to claim 1, wherein the ultrasound application varies between a one-half cycle and a continuous wave.

11. The method according to claim 1, wherein the ultrasound application is pulsed, intermittent, comprises rest periods of zero ultrasound energy across a time frame, or is continuous.

12. The method according to claim 1, wherein the ultrasound is applied at a repetition rate that varies from 1 microsecond to 1 second.

13. The method according to claim 1, wherein the ultrasound application comprises providing a pressure amplitude that varies from 100 kPa to 25 MPa.

14. The method according to claim 1 wherein the delivering the activated perfluorocarbon emulsion comprises systemic administration of the activated perfluorocarbon emulsion into a blood stream.

15. The method according to claim 14, wherein the systemic administration comprises intravenous administration.

16. The method according to claim 1, wherein the delivering the activated perfluorocarbon emulsion comprises delivery through a port in the catheter of the catheter-based system.

17. The method according to claim 16, wherein the port is distal to one or more ultrasound transducers located on the catheter of the catheter-based system.

18. The method according to claim 1, wherein the delivering the activated perfluorocarbon emulsion takes place prior to or at a same time as initiation of a reperfusion therapy to the patient.

* * * * *